United States Patent [19]

Fedor et al.

[11] Patent Number: 5,206,518
[45] Date of Patent: Apr. 27, 1993

[54] ACCELERATED WEATHERING APPARATUS

[75] Inventors: Gregory R. Fedor, Bay Village; Douglas M. Grossman, Fairview Park, both of Ohio

[73] Assignee: Q-Panel Company, Cleveland, Ohio

[21] Appl. No.: 801,715

[22] Filed: Dec. 2, 1991

[51] Int. Cl.$^5$ .............................................. G01N 17/00
[52] U.S. Cl. .......................... 250/504 R; 250/492.1; 250/493.1; 250/494.1
[58] Field of Search ............ 250/504 R, 492.1, 493.1, 250/494.1; 34/4

[56] References Cited

U.S. PATENT DOCUMENTS

| | | | |
|---|---|---|---|
| 3,576,125 | 4/1971 | Kockott et al. | 73/15 |
| 4,544,995 | 10/1985 | Suga | 362/225 |
| 4,665,627 | 5/1987 | Wilde et al. | 34/4 |

OTHER PUBLICATIONS

Advertising Brochure for Atlas Ci35 Fade-Ometer ®.
Advertising Brochure for Haraeus Xenotest ® 1200 CPS.

Primary Examiner—Jack I. Berman
Attorney, Agent, or Firm—Fay, Sharpe, Beall, Fagan, Minnich & McKee

[57] ABSTRACT

A Weathering apparatus having a light source which irradiates onto specimens located in a specimen supporting wall which is located on a side of a test chamber. The output of the light source is controlled by independently adjustable control channels. Each of the control channels include a light source detector inserted into the test chamber, control circuitry, and ballasts connected to the light sources. The light sources are controlled by the control channels to deliver an output equivalent to a desired set-point. In order to disperse light in an even manner to the specimens, a barrier is provided which interferes in a predetermined pattern with the passage of light produced by the light sources. The apparatus includes a calibrating device which automatically transfers an irradiance signal from a reference detector selectively positioned immediately adjacent the light source detector. The calibration signal is sent to the controller where the re-calibration of a selected control channel is accomplished.

21 Claims, 9 Drawing Sheets

FIG. 1
(PRIOR ART)
FIG. 2
(PRIOR ART)
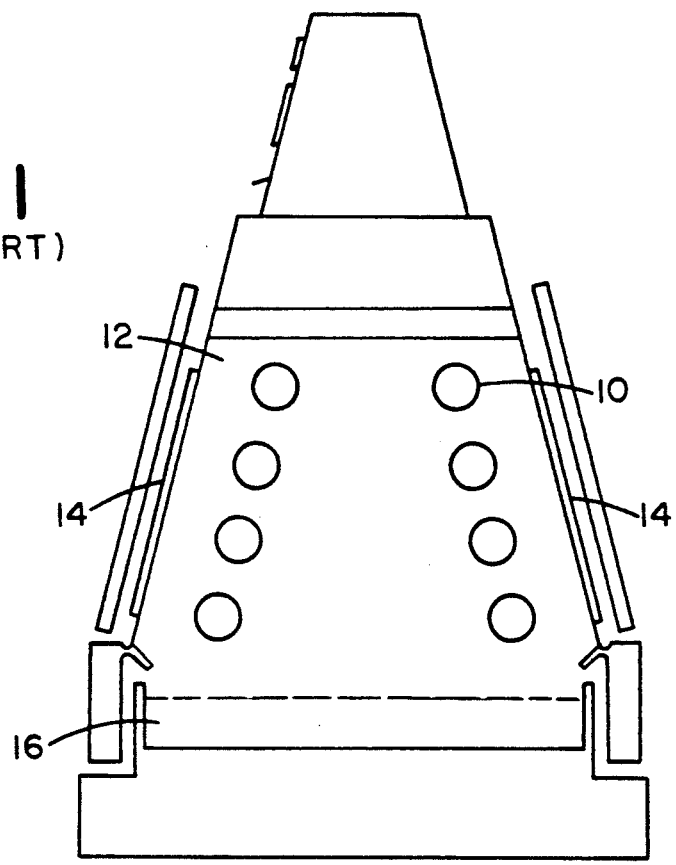
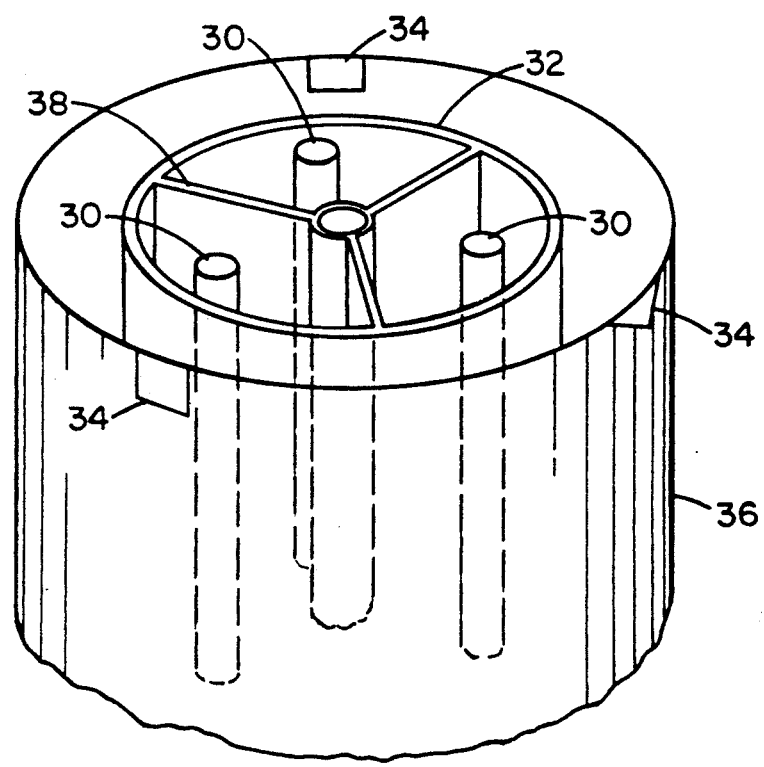

ACCELERATED WEATHERING APPARATUS

BACKGROUND OF THE INVENTION

This invention pertains to the art for testing specimens for fastness and deterioration under light, and more particularly, to such an apparatus using discharge lamps as light sources.

This invention is particularly applicable to testing of specimens using fluorescent ultraviolet lamps to simulate the deterioration caused by sunlight and will be described with particular reference thereto. However, it will be appreciated that the application has broader applications and may be advantageously employed in apparatuses using xenon lamps and in connection with many other accelerated weather testing concepts and uses.

A conventional testing apparatus using discharge lamps as shown in FIG. 1 has eight ultraviolet fluorescent lamps 10 provided in a test chamber 12 and arranged into symmetric downwardly divergent rows when viewed in cross-section. Specimens 14 to be tested are attached to two opposite specimen supporting walls of the housing of the test apparatus so as to face inwardly toward the fluorescent lamps and receive the light irradiance therefrom. In the machine shown, there are two specimens, an upper and lower one. However, there may be only a single specimen or more than two. The rear surfaces of the specimens 14 are exposed to the atmospheric air outside the machine. Outside air is heated and blown into the interior of the chamber 12 to regulate the temperature in the chamber 12. Water in moisture supply tank 16 is made hot and evaporated to supply moisture into the chamber 12.

In the above-described testing machine, one example of the machine's operation includes applying ultraviolet rays to the specimens 14 at a temperature of 60° C. for 16 hours and the fluorescent lamps 10 are turned off and the interior of the chamber 12 is kept at 50° C. for eight hours. These two steps, which constitute one cycle of a deterioration testing operation, are repeated continuously. While the fluorescent lamps are off, the humidity in the chamber 12 is high, and the rear surfaces of the specimens are exposed to the outside air at a low temperature. Accordingly, the surface of the specimens are wetted due to condensation. Thus, the wetting of the specimens, the applying of ultraviolet rays, and the drying are repeated, which speeds the deterioration of the specimens. It is to be appreciated that the above description is just one type of cycle for which machines of this nature can be used.

Problems, however, exist with the apparatus shown in FIG. 1. Initially, there is no provision for sensing the output of the fluorescent lamps 10, in order to track their rate of degradation. A normal procedure for attempting to provide a uniform output from the lamps, in such a device, is to rotate the positions of the lamps at predetermined time intervals in a predetermined sequence. Testing of the lamps to detect actual output is not provided, rather, assumptions are made as to the likely output, and the rotation sequence is made in consideration of the assumptions.

An additional drawback of this type of device is that the discharge lamps 10 which are located on one side of the chamber 12 transmit light beams to the opposite side of the chamber. For example, the row of lamps on the left side of the chamber in FIG. 1 are intended to produce irradiance for the specimen 14 also on the left side of the chamber. However, these lamps also produce beams in an undesirable fashion on the specimens 14 On the right hand side of the chamber 12. These undesirable beams tend to concentrate towards the middle of the specimen supporting wall. Therefore, a common problem is having the specimens which are located nearest the middle of the testing apparatus receiving higher doses of irradiance than those specimens arranged toward the top or bottom of the apparatus. This decreases the uniformity with which irradiance is transferred to the specimens.

Various attempts have been made to improve on the above-noted drawbacks of the conventional testing apparatus shown in FIG. 1. Among these is an apparatus from Atlas Electric Devices Company, called Atlas Ci35 FADE-OMETER ®; an apparatus from Heraeus called XENOTEST ® 1200 CPS; U.S. Patent to Suga, U.S. Pat. No. 4,544,995 issued Oct. 1, 1985; and U.S. Patent to Kockott, et al., U.S. Pat. No. 4,544,995 issued Apr. 27, 1971.

The Atlas device is arranged for use with a xenon arc lamp and includes a closed loop irradiance monitor as its primary light control system. The monitor, using a light pipe, interference filter and photosensitive diode feeding into solid state electronics, maintains predetermined irradiance levels and totalizes the energy received by the samples through an integrator. This device is also equipped with manual irradiance controls for use when periodically calibrating the system.

The apparatus from Heraeus is also directed for use with xenon arc lamps. This device employs three light detectors to detect the output of three individual xenon arc lamps.

A conventional apparatus including elements of these two above-discussed devices is shown in FIG. 2. In this Figure, discharge lamps 30 which can be of a xenon type, are vertically disposed. A filter 32 surrounding the discharge lamps 30 is provided to allow only desired wavelengths of light to pass. Sensors 34 are provided to sense the output of the vertically positioned discharge lamps 30, and a rotating specimen holding rack is positioned to encircle the discharge lamps 30. Each of the detectors 34 are provided to detect the irradiance produced from a respective discharge lamp 30 over time. The rotating specimen holding rack 36 rotates the specimens located in the specimen holding rack 36. The sensors 34 are provided to track the output of the discharge lamps 30, and the rotating specimen holding rack 36 attempts to provide each of the specimens with an average overall equal amount of irradiance. Inner walls 38 are used to direct reflective light of the discharge lamps 30 outward to the specimens.

Another device, employing ultraviolet lamps in an arrangement similar to FIG. 1, is known to include a single sensor. However, in such an arrangement it is necessary to match the characteristics of the lamps prior to placing them in such a device. This is required since the sensor will only sense the lamps closest to its location. Thus, the sensor will assume the lamps placed distant from it are operating the same as the lamps it actually senses.

The Suga patent attempted to improve on the prior art device shown in FIG. 1 by adjusting the alignment of the row of discharge lamps 10 of FIG. 1 into a non-symmetric arrangement. This arrangement is shown in FIG. 3. As noted in this Figure, the discharge lamps 10 are not disposed immediately below each other. Rather, they are in a specifically positioned arrangement. This was done in Suga in an attempt to provide irradiance to the samples 14 with a more uniform distribution. The numeral designations shown in FIG. 3 are millimeter (mm) measurements.

The Kockott, et al. patent is directed to a device using an elongated source of irradiation inside a cylindrical carrier surface. Kockott, et al. discloses three approaches to provide a uniform distribution of irradiance to the samples. First, mirrors 14 are arranged to reflect usable light; second, a light source 20 is designed to increase light intensity at its ends; and, third, collimating discs 24 are used to inhibit divergence of the radiation emitted from the source.

While the above-discussed references provide some improvements upon the conventional apparatuses shown in FIG. 1 and FIG. 2, drawbacks still exist.

With particular attention to the Atlas and Heraeus devices, it is noted that both use a rotating specimen rack arrangement. This rack is necessary for a very basic reason. The Atlas device includes a monitoring system which monitors the overall output of the xenon arc lamp in order to attempt to maintain a predetermined total irradiance output level over time for the entire system. The Heraeus device uses three sensors to control the three different lamp's output over time. These sensor arrangements are used to produce an irradiance which is constant over time. However, neither of these devices use a sensing arrangement to make irradiance constant over space.

Both of the devices use a rotating specimen rack in an attempt to achieve spatial uniformity. Therefore, spatial uniformity which is achieved, is accomplished by having the specimens in the rotating rack revolve around the lamps, so the effective light dosage received by each specimen is an average of the different irradiances at each point on the circumference of the sample plane. Though rotating the rack increases uniformity, it also increases the complexity of the device by requiring a motor and associated rotation mechanisms.

Thus, even though these devices include irradiance sensing capabilities, they implement these capabilities only for a consistent output over time, not space. As can be seen in FIG. 2, due to the geometry of the devices, there is a different irradiance at every point around the circumference of the sample plane. Therefore, areas which are located in front of a discharge lamp 30 will have a high irradiance area H while samples which are at a position distant from a discharge lamp 30 will receive lower L irradiance. Rotation of the rack attempts to produce an overall average uniformity of irradiance impinging upon samples.

The known ultraviolet system using a single sensor includes the drawback of needing to match the lamps being used in the system. This requires extensive testing of the lamps prior to use. A further drawback is that in such a system, when a lamp located distant from the sensor location burns out or degrades, the decrease in its output will not be sensed. This is true as only the nearest lamps are actually sensed and an assumption is made that the remaining lamps are functioning in a similar manner.

The Suga patent attempts to increase the uniformity of light impinging upon specimens by moving the center two lamps away from the samples to increase uniformity of light to the samples from top to bottom. A drawback of such an arrangement is that it is not possible to easily retrofit existing weathering devices to gain whatever improvement there may be from the Suga arrangement.

A drawback to the Kockott, et al. patent is that it is directed to single lamp systems. Another drawback to Kockott, et al. is that it increases the complexity and cost of the apparatus.

A further drawback associated with the conventional testing apparatuses as discussed above is their calibration. These devices require manual manipulations by an operator which in turn means the operator is required to make decisions which are critical to proper calibration. Since the operator is responsible for making decisions while manually re-calibrating the apparatus, the accuracy of the calibration will be dependent upon the skill of the operator. Additionally, since the calibration is accomplished manually, extended down time occurs during such calibration and there exists a substantial possibility of inaccuracies due to operator error.

The subject invention contemplates a new and improved accelerated weathering apparatus that overcomes all of the above referenced problems and others and provides an easily assembled, reliable testing structure.

SUMMARY OF THE INVENTION

According to the present invention, there is provided an improved accelerated weathering apparatus. The apparatus includes a housing with a test chamber and a specimen supporting wall located on a side of the chamber. A light source is provided in the test chamber. A ballast arrangement is connected to the light source for controlling the amount of power the light source receives from a power source. A controller is connected to the ballast arrangement, to produce a ballast control signal for controlling operation of the ballast arrangement according to a desired set-point value. A light source detector is inserted in the specimen supporting wall in order to detect irradiance existing in the test chamber so the light source detector can generate an irradiance signal which is then input to the controller. The controller uses the irradiance signal to adjust the ballast control signal to maintain the selected set-point value. A calibration portion includes a reference detector designed to detect the irradiance inside the test chamber and to produce a reference irradiance signal. The reference irradiance signal is transmitted to a calibration meter which produces a calibration signal. The calibration signal is transmitted to the controller for calibrating the apparatus.

According to another aspect of the invention, the accelerated weathering apparatus includes a barrier configuration located within the test chamber. The configuration is composed of material which selectively blocks and diverts beams of light produced by an array of light sources. The blocking and diversion of the beams is made to occur in a pattern selected to increase an even distribution of the beams to the specimen supporting wall.

According to another aspect of the present invention, in the accelerated weathering apparatus the light source is a plurality of individual light sources and the device also includes a plurality of concurrently operating automatically adjusted control channels for controlling output of the individual light sources. The channels control the output of at least one of the light sources.

In a more limited aspect of the apparatus, each of the channels include a ballast, a control device, and a light source detector. The ballast is connected to at least one of the light sources to control the amount of power the light source receives from the power source. The control device is connected to the ballast and produces a ballast control signal to control the operation of the ballast device. The light source detector is inserted into the specimen supporting wall at a location corresponding to an associated light source, in order to detect irradiance existing in the test chamber produced by the light source. The detector also generates an irradiance signal, representative of the detected irradiance, which is transmitted to the control device. The control device uses the irradiance signal to adjust the ballast control signal in order to maintain a selected value.

One advantage of the present invention resides in its ease of operation and accuracy. In particular, many of the tasks previously required to be performed by an operator are now removed from operator control and performed automatically, thereby reducing the possibility of operator error. The preferred embodiment adjusts the output of the lamps to a desired set-point and calibrates the apparatus in response to the actuation of a switch by the operator. Thus there is no need for the operator to manually calibrate the apparatus or adjust the output of the lamps.

Another advantage of the present invention resides in the improved accuracy with which the calibration procedure is performed.

Another advantage of the present invention resides in controlling the light beam distribution within the test chamber. Such control increases the uniform distribution of beams to all of the specimens in the specimen wall.

Still yet another advantage of the present invention resides in individual channel control of the light sources. By using a plurality of detectors and a plurality of channels to control the output of the light sources a uniformity over time and uniformity over space of irradiance within the test chamber is achieved. This is accomplished by assuring that each of the individual channels have equivalent outputs.

An additional benefit of the plurality of channels controlling the light sources is that as the output from a particular light source degrades the ballast can be signaled to boost output of that particular light source. Thus, since an operator can observe the displayed output value of each channel and replace light sources when the desired output can no longer be achieved, an increase in the useful life of a light source is accomplished. Therefore, if only one light source is burned out, it can be replaced without replacing all of the light sources.

Still yet another advantage of the present invention resides in the implementation of internal calibration circuits of the calibration meter which are selectable by a switch such as a pushbutton. This allows accurate calibrations to be made on different types of light sources, without the necessity of changing the reference detectors or the calibration of the calibration meter. Such a change would otherwise be necessary since a detector's response will vary depending on wavelengths received, and different light sources will produce different wavelengths even at equal outputs. For example, a UV-A lamp will cause a larger signal to be detected by a sensor than a UV-B lamp at the same output since a UV-A lamp has a longer wavelength.

Still further advantages of the present invention will become apparent to those of ordinary skill in the art upon reading and understanding the detailed description of the preferred embodiment.

BRIEF DESCRIPTION OF THE DRAWINGS

The invention may take form in various parts and arrangements of parts and in various steps and arrangements of steps. The drawings are only for purposes of illustrating a preferred embodiment and are not to be construed as limiting the invention.

FIG. 1 is a schematic sectional end view of a conventional testing apparatus;

FIG. 2 is a schematic side view of a conventional testing apparatus using a rotating specimen rack;

DETAILED DESCRIPTION OF THE PREFERRED EMBODIMENT

Figure 3:
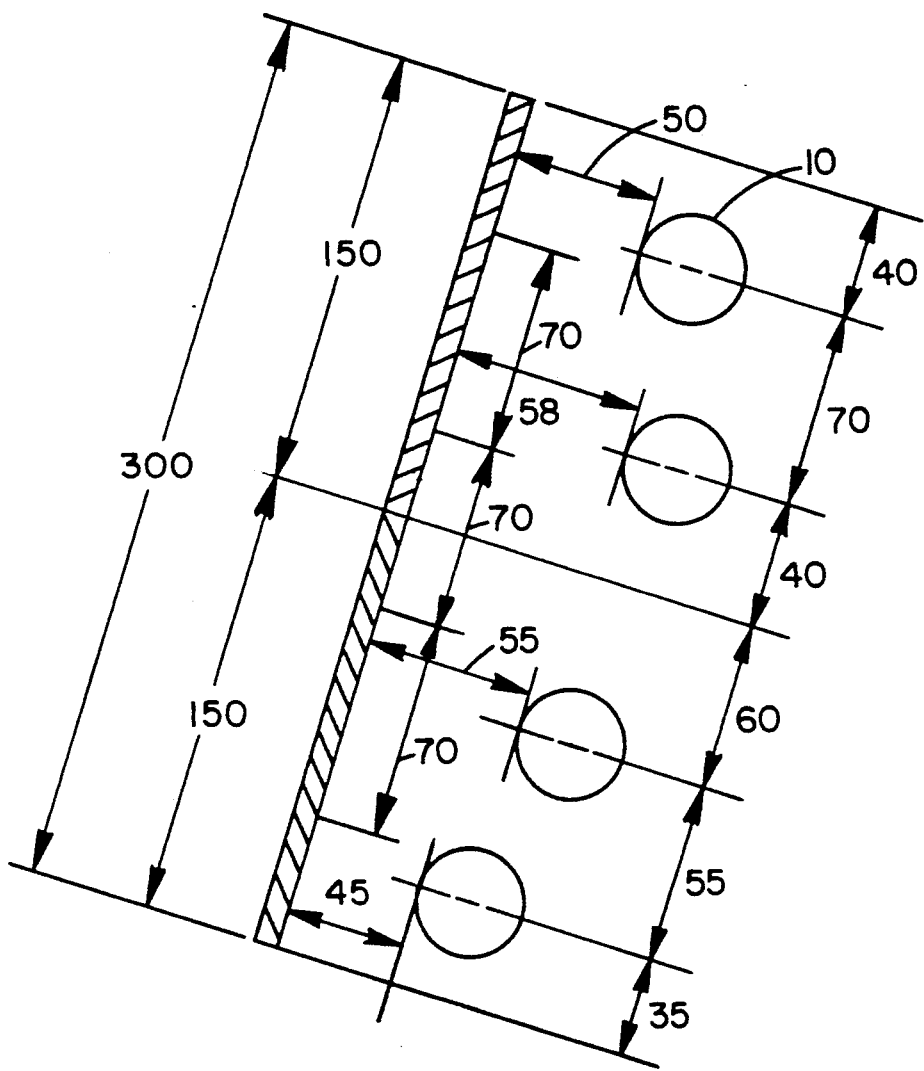
FIG. 3 is a diagram of a known arrangement of lamps in a conventional testing apparatus.
Figure 4:
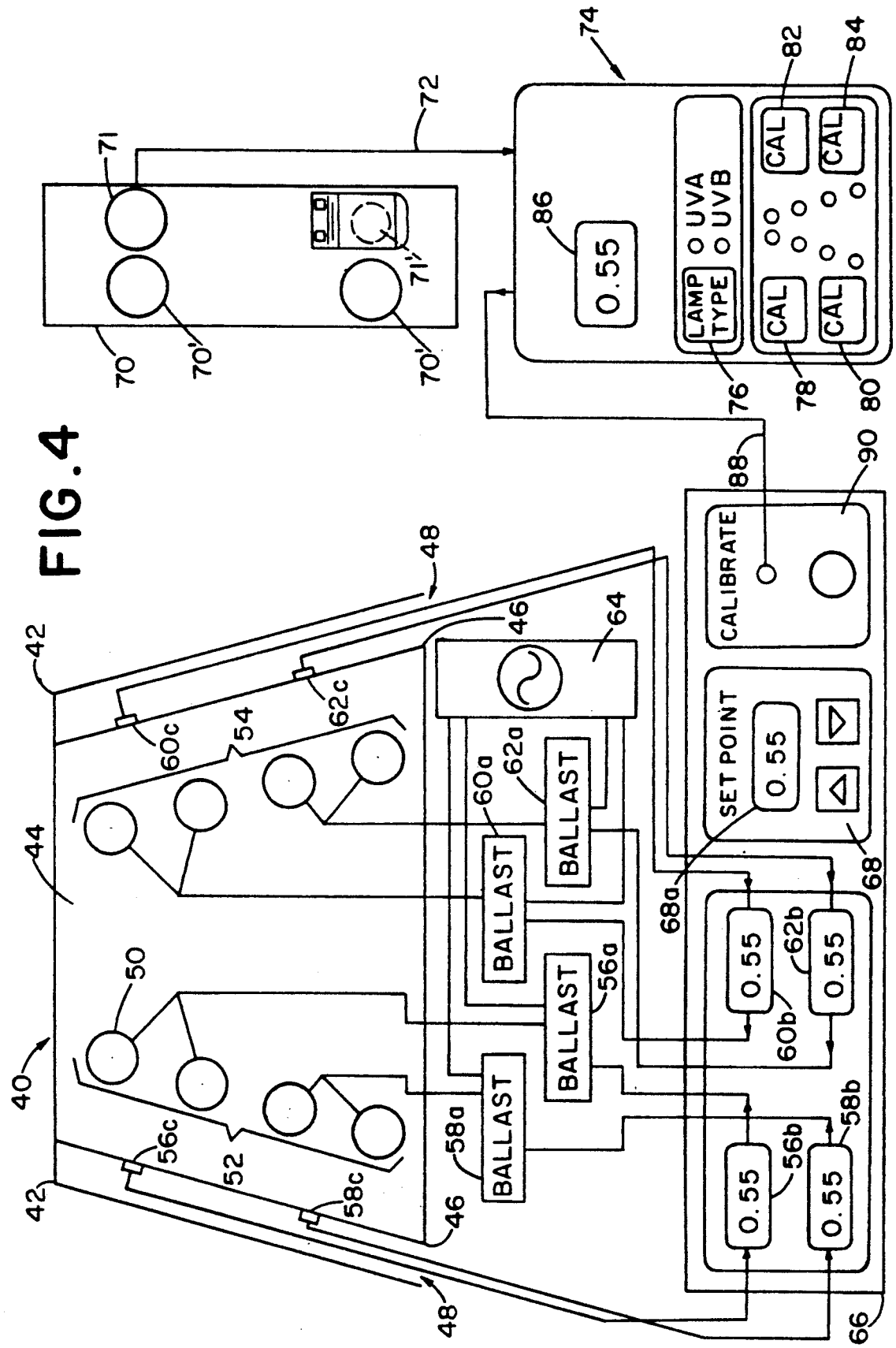
FIG. 4 is a diagrammatic illustration end view of an accelerated weathering apparatus in accordance with the present invention showing the features of multi-channel control and calibration.

With reference to FIG. 4, an accelerated weathering device is shown which includes a housing 40 with outer panels 42 for enclosing a test chamber area 44. Downwardly and outwardly inclined specimen supporting walls 46 are located on opposite sides of the test chamber 44. Air gaps 48 located between the outer panels 42 and the specimen walls 46 allow for air flow to cool the backsides of specimens.

Within the test chamber 44 is a light source such as eight ultraviolet fluorescent lamps 50 divided into two rows 52 and 54 each having four fluorescent lamps 50.

Several types of fluorescent ultraviolet lamps can be used in the present apparatus. The particular application determines which lamp should be used. The lamps differ in total amount of ultraviolet energy emitted and in their wavelength spectrum.

Fluorescent lamps are usually categorized as UV-A or UV-B lamps, depending on the wavelength region into which most of their light output falls. The ultraviolet spectrum is divided into three wavelength regions, the UV-A region from 315 to 400 nanometers (nm), the UV-B region from 280 to 315 nm, and the UV-C region, below 280 nm.

The UV-B region includes the shortest wavelengths found in sunlight at the earths surface and is responsible for most polymer damage. Fluorescent UV-B lamps are the most widely used lamps for simulating the damage caused by outdoor sunlight. For many applications, they are the fastest and most cost-efficient lamps.

For certain applications, the longer wavelength spectrum emitted by UV-A lamps is used. UV-A's are especially useful for tests comparing generically different types of polymers. Because UV-A's have no UV output below the solar cutoff of 295 nm, they usually do not degrade materials as fast as UV-B lamps. But they give a correlation with actual outdoor weathering results.

The ultraviolet lamps 50 are connected in pairs to a plurality of ballasts 56a-62a. The ballasts control the power supplied to the ultraviolet lamps 50 delivered from a power source 64.

The ballasts 56a-62a are part of four individually adjustable control channels. A controller 66 includes control circuitry which is part of the control channels. These individually adjustable control channels further include displays 56b-62b, and light source detectors such as ultraviolet detectors 56c-62c. The ultraviolet detectors 56c-62c are inserted into the specimen holding walls 46 at positions where it is most beneficial for detection of the irradiance generated by the pair of the ultraviolet lamps controlled by a corresponding control channel. In particular, the detectors are placed generally midway between the two lamps of a pair.

In the preferred embodiment the holding walls 46 are comprised of specimen panels which hold the individual specimens, and a frame into which the panels are placed. Additionally, detector panels such as detector panel 70 are provided for holding the detectors 56c-62c. Each detector panel 70 includes four openings, two of the openings 70', which are vertically distanced from each other, are for ultraviolet detectors, and the additional two openings 71', which are immediately adjacent to the ultraviolet detector openings, are for a reference detector 71 when calibrating an associated control channel.

A set-point control 68 is provided to generate and transfer a set-point value at which the control channels (56a-62a; 56b-62b; 56c-62c; 66) of the device are to operate, this set-point value is reflected on set-point display 68a.

The reference detector 71 in one embodiment can be of the cosine response receptor type, which accurately detects irradiance according to the cosine angle of the light impinging upon it. The reference detector 71 transmits a detected reference irradiance signal 72 to a calibration meter 74. The calibration meter 74 includes a selector switch 76 for selecting between operations for calibrating lamps of UV-A or UV-B types. Four channel selection switches 78-84 make it possible for an operator to individually calibrate each of the control channels. A calibration display 86 displays the value of a calibration signal (in units of $W/m/nm^2$ at $\lambda$ nm) which is generated from the detected reference irradiance signal 72. A calibration signal 88 is transmitted automatically to a calibration input 90 connected to, or which is part of the controller 66.

When it is desired to calibrate any of the control channels the reference detector 71 is inserted into a reference detector opening 71' in the appropriate detector panel which is in one of the specimen holding walls 46. The reference detector opening 71' may include a cover which is opened to insert the reference detector 71 therein.

Figure 5:
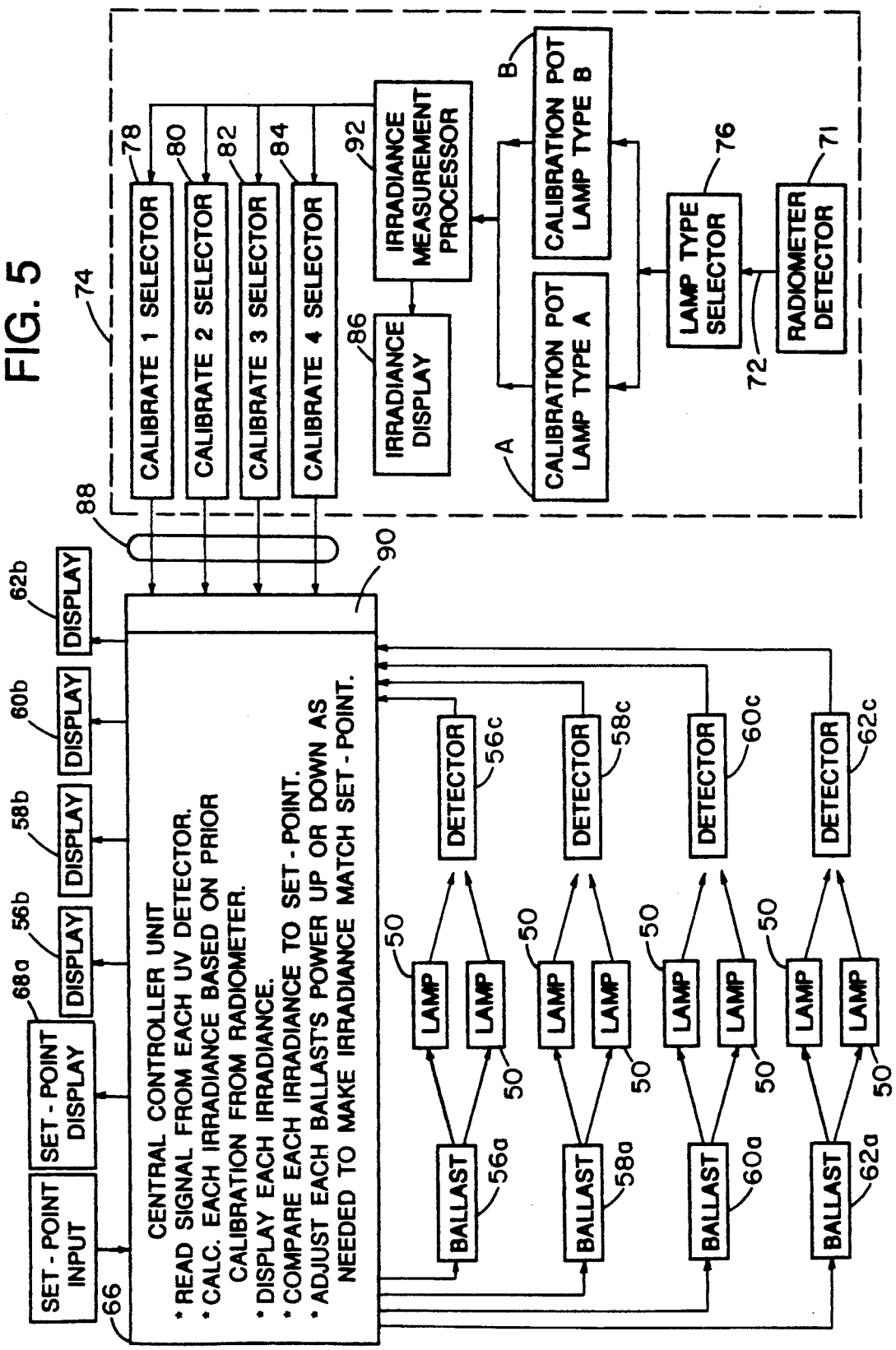
FIG. 5 is a logical schematic of the diagrammatic illustration of FIG. 4, of a preferred embodiment of the accelerated weathering apparatus in accordance with the present invention.

FIG. 5 is a logical schematic which shows the apparatus in an alternative representation format. This format while reflecting what is shown in FIG. 4 additionally discloses that two calibration potentiometer circuits, type A and type B, are included within the calibration meter 74. Dependent upon which lamp type is selected by selector 76 a particular potentiometer arrangement will be used. The calibration meter 74 in FIG. 5 further shows that an irradiance measurement processor 92 is used to convert the detected reference irradiance signal 72 into a value for use on display 86. Additionally, the processor 92 develops the calibration signal 88 which is transmitted to the calibration input 90.

Figure 6A:
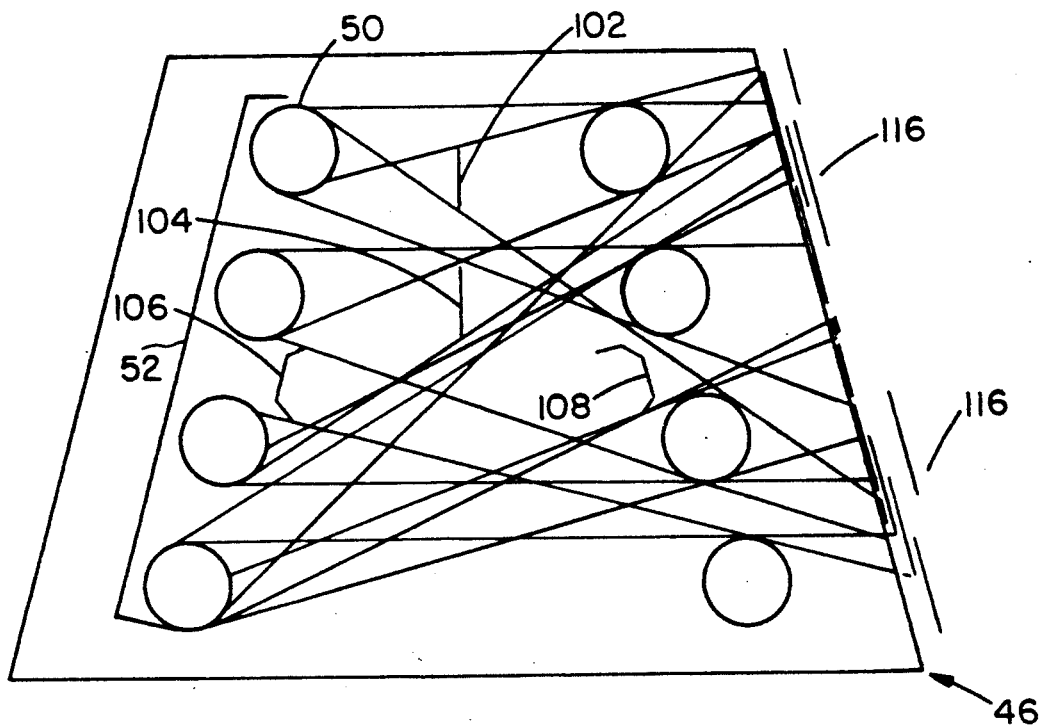
FIGS. 6A–6B are preferred embodiments of the barrier feature of the accelerated weathering apparatus in accordance with the present invention.
Figure 6B:
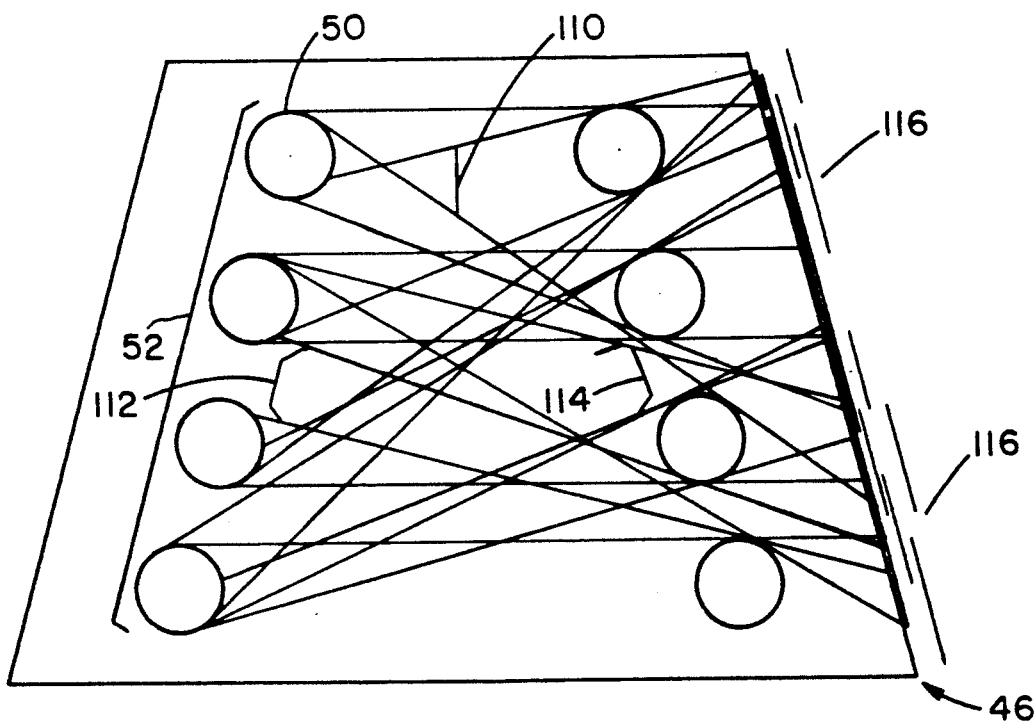

FIGS. 6A and 6B show preferred embodiments of the barrier arrangements used to increase the uniformity of irradiance distributed to the specimens. In order to simplify the discussion with reference to FIGS. 6A-6B, only light beams emitted from the ultraviolet lamps in row 52 are shown. Thus for this discussion the irradiance is only impinging upon the specimens on the right side specimen wall 46. With particular attention to FIG. 6A, a more uniform distribution of irradiance is achieved by placement of a material used to interfere with the random beam pattern by deflecting and/or blocking beams from the fluorescent lamps of row 52. The particular arrangement includes vertical strips 102 and 104 and light bars 106 and 108. The placement of this diverting and blocking material causes the beams emitted from the fluorescent lamps 50 to be directed to the upper and lower portions of the specimen wall 46. When no barrier arrangement is included the middle portion of the specimen wall 46 receives the highest percentage of light beams from the lamps located on the opposite side of the chamber, thereby providing uneven distribution of irradiance to the specimens.

FIG. 6B shows a second embodiment of the present barrier arrangement. In this embodiment a first vertical material 110 and light bars 112 and 114 are implemented.

It should be noted that the vertical lines 116 shown on the specimen wall 46 of the device are intended to represent the spatial distribution of the beams of light being directed towards the associated section of the wall 46, from the lamps on the opposite side of the test chamber. As can be seen in FIGS. 6A and 6B the inclusion of the barrier devices in the preferred embodiments direct the light beams in a more desirable pattern to the upper and lower regions of the chamber. Thus, the disclosed arrangement of these barriers improve the distribution of light beams developed by the opposite side row of ultraviolet lamps.

Figure 7:
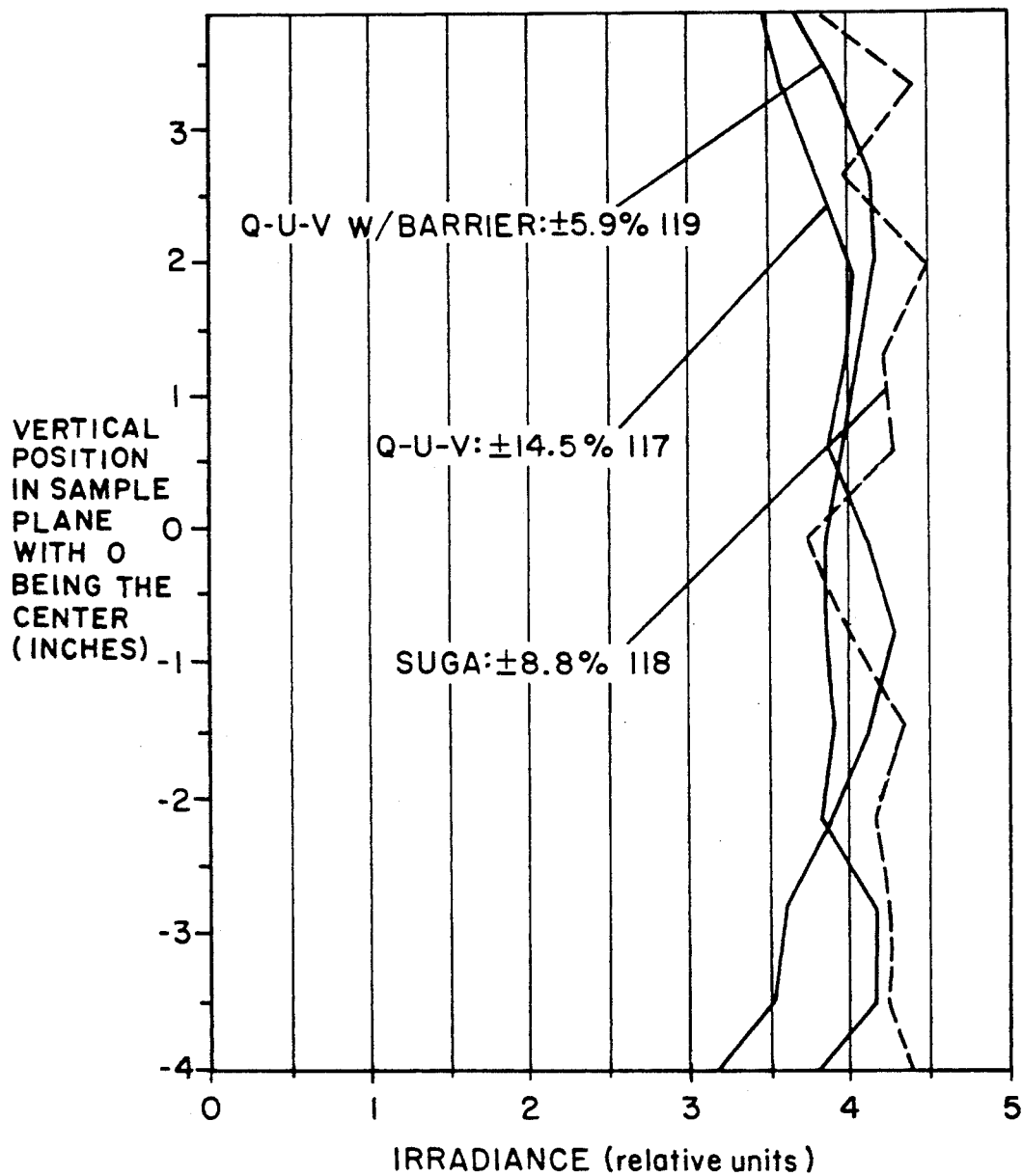
FIG. 7 is a graph showing results of testing of irradiance distribution in various situations.

FIG. 7 is a graph reflecting data in a test chamber similar to that of the preferred embodiment of the present invention. The data reflects three situations. The first is when no barrier arrangement is used within the test chamber 117; second, when an arrangement of the lamps are provided similar to that shown by Suga 118; and third, when a barrier arrangement corresponding to the preferred embodiment shown in FIG. 6A 119, is implemented. The results disclosed by such testing show that there is a ±14.5% deviation of irradiance from the top of a standard sample plane to the bottom of a standard sample plane, for a sample plane which is 8 inches in its vertical position. When the arrangement of the lamps in Suga is implemented, there is a ±8.8% deviation from the top of the standard sample plane to the bottom. When an apparatus of the present invention uses a barrier arrangement as shown in FIG. 6A, there is a ±5.9% deviation from the top to the bottom of the standard plane.

Figure 8:
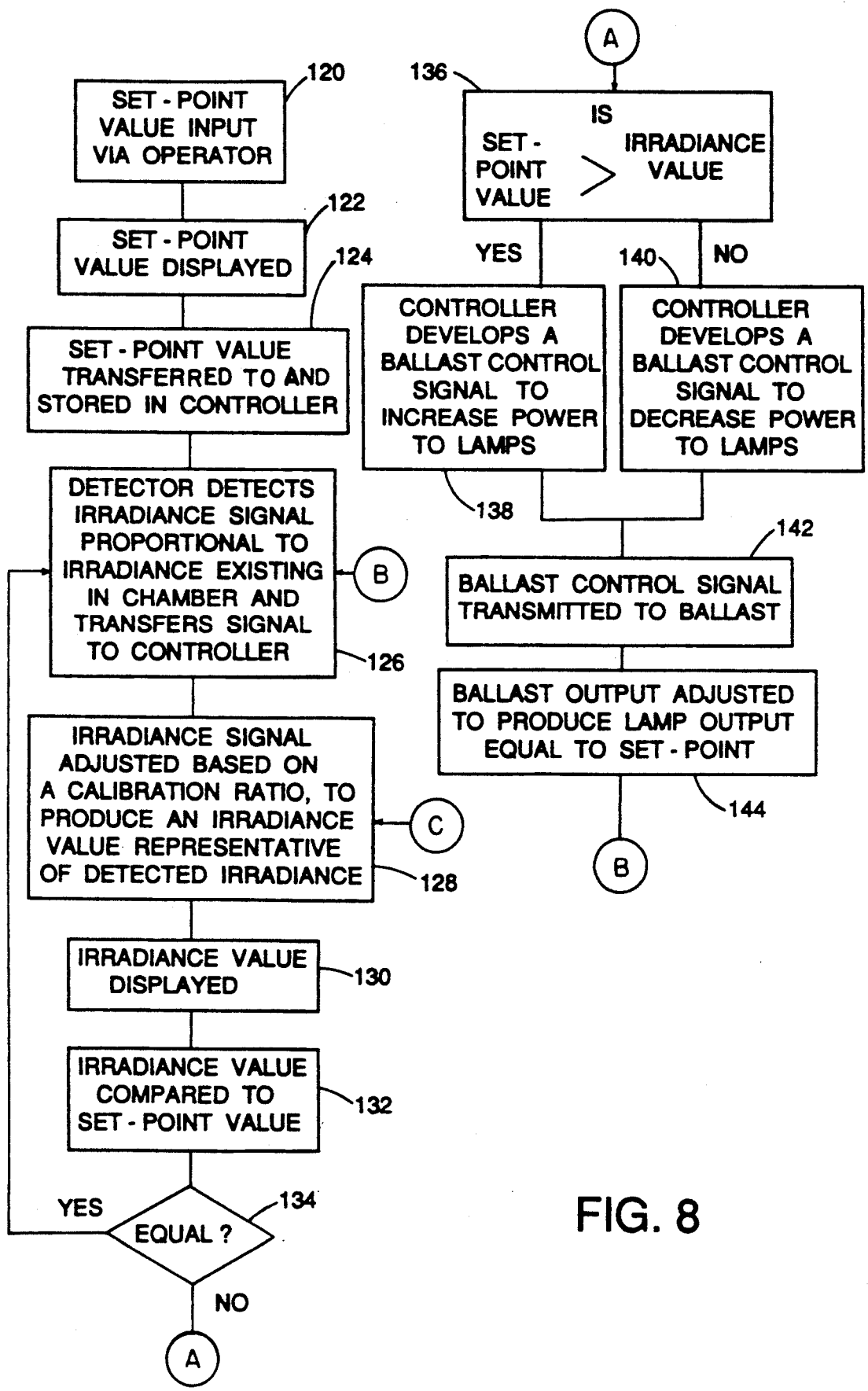
FIG. 8 is a flow chart illustrating the operation of one channel of the multi-channel feature of the present invention.

With attention to FIGS. 8 and 9, the operational procedure of the accelerated weathering apparatus shown in FIGS. 4–5 will be discussed. In particular, in FIG. 8 an operator enters a set-point value 120. This set-point value is displayed on a display device 122. The set-point value is also transferred to, and stored in the controller 124. Detectors detect irradiance existing in the test chamber due to output of the ultraviolet lamps, and a detected irradiance signal proportional to irradiance in the chamber is transferred to the controller 126. Control circuitry of the controller calculates an irradiance value which is representative of the detected irradiance 128 This calculation operation includes the use of a calibration ratio which is stored in the controller. Thereafter, the irradiance value is displayed on the selected channel display 130. This irradiance value is compared to the previously entered set-point value 132 and it is determined whether or not these values are equal 134. If the values are equal the above process is cycled beginning with detection of irradiance existing in the test chambers 126–134.

If, on the other hand, the irradiance value and the set-point value are not equal a determination is made as to whether or not the set-point value is greater than the irradiance value 136. When the set-point value is greater than the irradiance value the controller develops a ballast control signal to increase the power which is sent to the lamps 138. If the set-point value is less than the irradiance value the controller develops a ballast control signal which decreases the power sent to the lamps 140. This ballast control signal is transmitted to the ballast 142. Responsive to this signal the ballast output readjusts so the output of the ultraviolet lamps are increased or decreased depending on the requirements necessary to maintain the set-point value 144. It is to be appreciated that the above discussion is similar for all four control channels and that the control channels are each concurrently monitoring the lamps 50 associated with each particular channel.

By having four individually adjustable control channels, it is possible to provide uniformity of irradiation to the specimens over both time and space. In particular, the detectors 56c–62c are capable of detecting when the irradiance is not of a desired value and the device can automatically readjust the power to the fluorescent lamps 50 in order to bring the output of the lamps 50 associated with a particular control channel to a desired level. Thus, each pair of fluorescent lamps, controlled by the control channels, are capable of outputting a consistent irradiance over an extended time period. When either of the lamps of the pair vary, the ballast output is adjusted to compensate for such deviation. Thus, a consistency in uniformity over time is accomplished.

Further, since there are a plurality of detectors arranged spatially in the apparatus, it is possible to provide for a uniformity over the area of the specimen wall 46. With particular reference to FIG. 4, if detector 56c detects an irradiance of too high a value or too low a value the output of the associated ultraviolet lamps 50 are adjusted to come within a desired set-point range. This adjustment will be made for all the lamp pairs of the respective control channels. Thus as shown in FIG. 4, control displays 56b–62b will show equal irradiance being detected. Thus, ultraviolet detectors 56c–62c are detecting the same irradiance values along the height of the specimen walls 46. If only a single detector were used in the present system there would be no uniformity over space, as the detector would be detecting only the light which existed at a single location which may or may not be representative of other locations in the test chamber.

Figure 9:
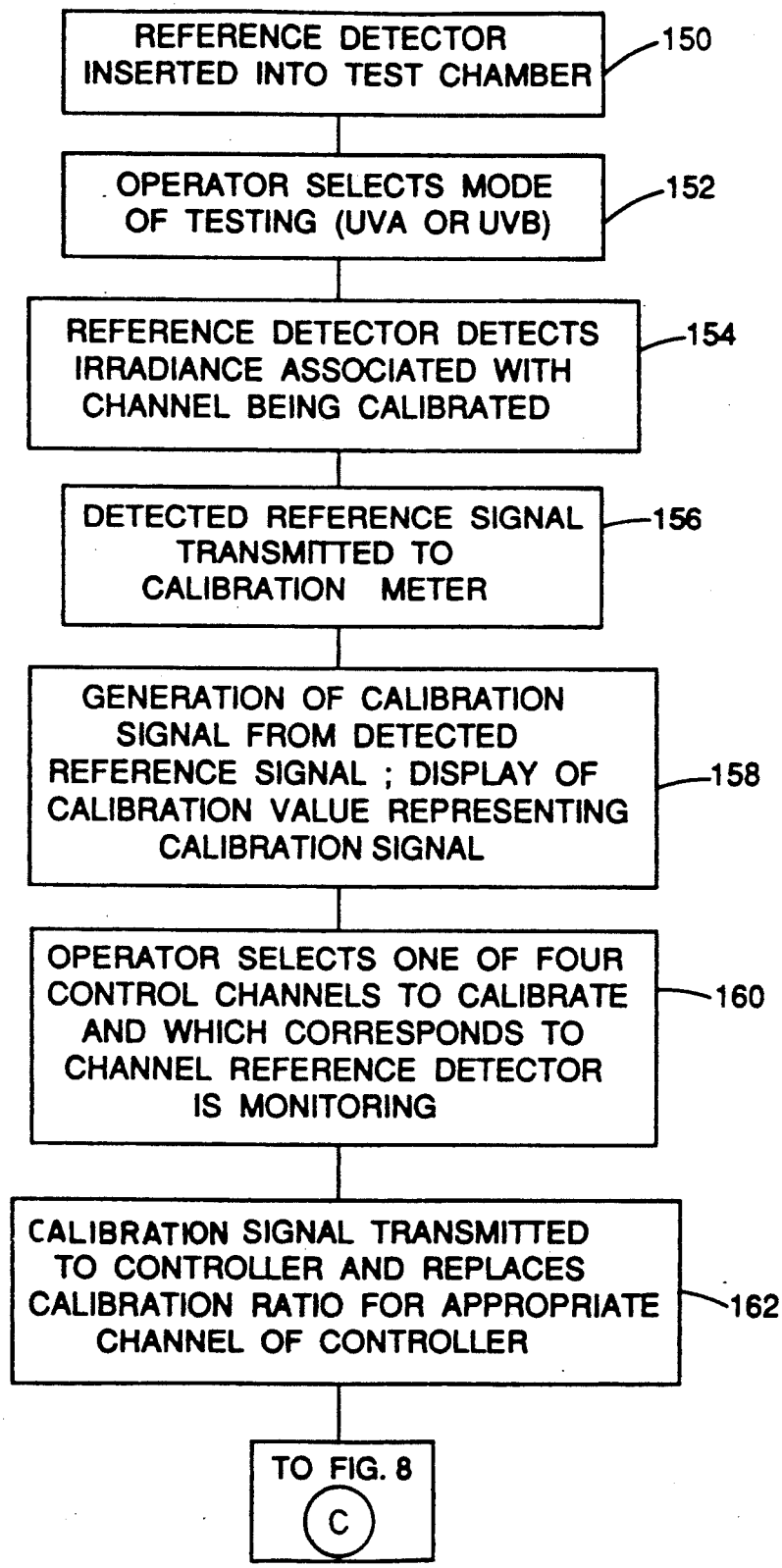
FIG. 9 is a flow chart showing a preferred embodiment of the calibration operation in accordance with the present invention.

With reference to FIG. 9, a discussion will now be had concerning the calibration of the apparatus shown in FIGS. 4 and 5. In particular, a reference detector is inserted into one of the openings or covered ports which are immediately adjacent to the ultraviolet detectors 150. The operator selects the mode of desired testing (i.e. UV-A or UV-B) 152. The reference detector detects the irradiance associated with the channel being calibrated 154 and a detected reference irradiance signal, representing the detected irradiance is transmitted to the calibration meter 156.

A calibration signal is generated from the detected reference signal by the irradiance measurement processor 158 and a calibration value representing the calibration signal is displayed. Next, the operator selects one of the four independent control channels 160 to be calibrated. The selected channel will correspond to the channel being monitored by the reference detector. The calibration signal is transmitted to the controller 162, and replaces the calibration ratio previously stored in the controller, which is used to adjust the irradiance signal detected by the ultraviolet detector of the selected channel. After this new calibration ratio has been transferred, the operation of the apparatus is transferred to step 126 of FIG. 8.

The irradiance value will then be equal to the set-point value indicating the channel is properly calibrated. When calibration of one channel is accomplished, the reference detector can be moved by the operator to another opening and another channel can then be tested, or the testing can be ended.

Figure 10:
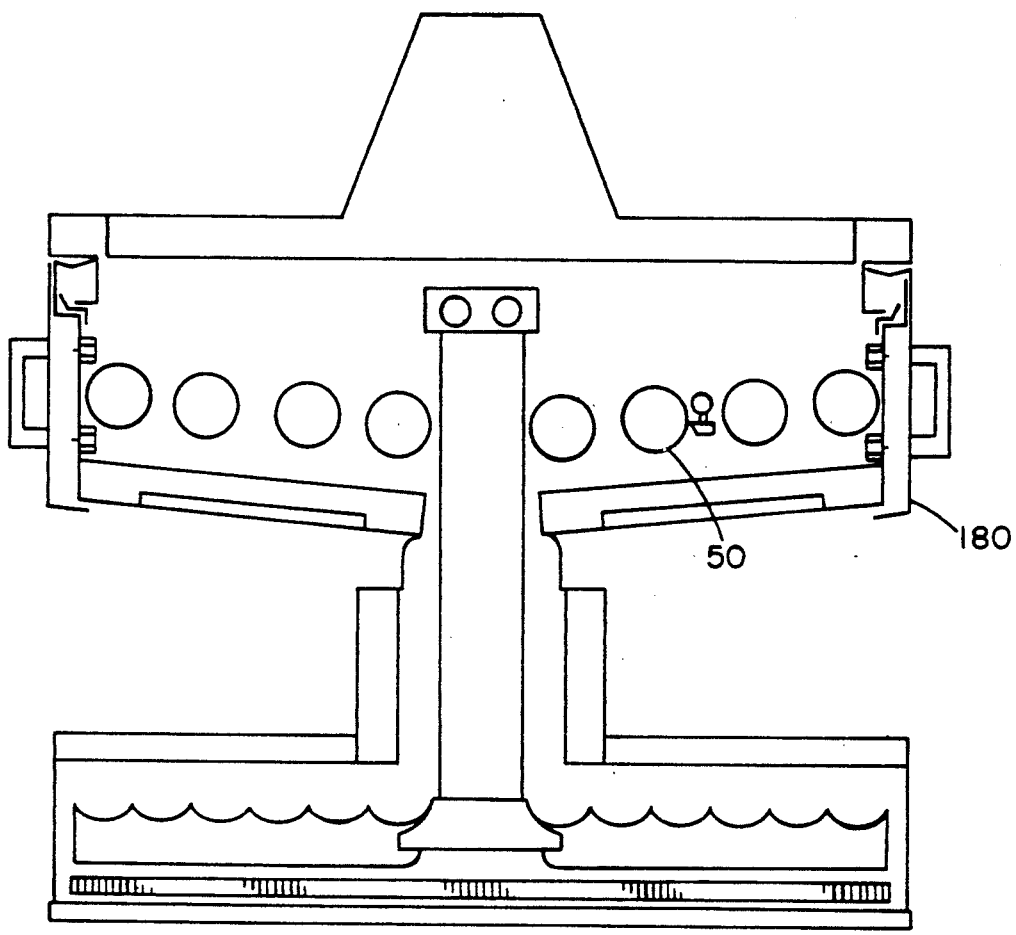
FIG. 10 is the present invention in an alternative embodiment wherein the specimen holding device is a horizontal specimen drawer.

FIG. 10 shows an additional embodiment to the present invention wherein the specimens are placed within a specimen drawer 180 rather than in a specimen holding rack 46. The drawer is substantially horizontal. The lamps 50 are arranged above the specimen drawer.

It is to be appreciated that the preferred embodiment can be altered to have more or less than eight ultraviolet lamps, have more or less than two lamps controlled by each control channel, and more than the four control channels. It is also possible to operate the device with only two or three control channels, however, refinement of the uniformity of time and space would degenerate somewhat, while increasing the number of lamps and control channels add to the space constraint problems.

It is to be further appreciated that the present invention can be used in systems using xenon and other discharge lamps. Elements of the invention such as the automatic calibration can be useful in single lamp systems and the lamp select button allows use of lamps of different spectrum distributions.

The invention has been described with reference to the preferred embodiment. Obviously, modifications and alterations will occur to others upon reading and understanding the proceeding detailed description of the preferred embodiment. It is intended that the invention be construed as including all such modifications and alterations insofar as they come within the scope of the appended claims or the equivalent thereof.

Having thus described the preferred embodiment, the invention is now claimed to be:

1. An accelerated weathering apparatus comprising:
   a test chamber;

a specimen supporting means for supporting specimens in the test chamber;

a light source located within the test chamber for producing light in the test chamber;

a power source for powering the light source;

a ballast means connected to the light source, for controlling the amount of power the light source receives from the power source;

a controller, connected to the ballast means, to produce a ballast control signal for controlling operation of the ballast means;

a set-point means connected to the controller for generating and sending a set-point signal to the controller, the set-point signal determining an initial set-point value of the ballast control signal;

a light source detector means inserted into the specimen supporting means for detecting irradiance existing in the test chamber, and for generating an irradiance signal representative of the detected irradiance;

an irradiance signal input means, for inputting the irradiance signal to the controller, the controller using the irradiance signal to adjust the ballast control signal, to maintain the selected set-point value;

a reference detector means designed to detect the irradiance in the test chamber and to produce a reference irradiance signal representative of the detected irradiance;

a reference irradiance signal transmitting means for transmitting the signal to the reference detector means;

a calibration meter arranged for receiving the reference irradiance signal and for producing a calibration signal; and, a calibration signal input means for inputting the calibration signal directly to the controller.

2. The accelerated weathering apparatus according to claim 1 further including:

a plurality of light sources; and, a barrier located within the test chamber, a barrier composed of a material which interferes with passage of light produced by the plurality of light sources in a pattern selected to increase uniformity of the light across each of the specimens attached to the specimen supporting wall.

3. The accelerated weathering apparatus according to claim wherein the calibration meter includes a transfer switch, which when activated automatically transfers the calibration signal from the calibration meter, through the calibration signal input means, to the controller.

4. The accelerated weathering apparatus according to claim 1, wherein the calibration meter includes at least two internal calibration means, which allows calibration of at least two different types of ultraviolet light while using the same reference detector means.

5. The accelerated weathering apparatus of claim 4, wherein the calibration meter calibrates for UV-A and UV-B ultraviolet fluorescent lamps.

6. The accelerated weathering apparatus according to claim 1, further including a covered reference detector opening in the specimen supporting means to hold the reference detector means.

7. The accelerated weathering apparatus of claim 6, wherein the calibrated ultraviolet detector is of a cosine response receptor type.

8. The accelerated weathering apparatus of claim 1, wherein the calibration meter is designed to be hand-held.

9. An accelerated weathering apparatus comprising:

a test chamber;

a specimen supporting means for holding a specimen in the test chamber;

an array of light sources located within the test chamber which produce light in the test chamber; and a barrier located within the test chamber, composed of a material which interferes with passage of the light produced by the light sources in a pattern selected to increase an even distribution of the light to the specimen held by the specimen supporting means.

10. The accelerated weathering apparatus according to claim 9, wherein the array of light sources include:

first and second rows of lamps each having a first uppermost lamp, a second lamp under the first lamp, a third lamp under the second lamp and a fourth lower most lamp, the barrier configuration including;

a first vertical strip of the material located midway between the uppermost lamps of the first and second rows, extending vertically from centers of the uppermost lamps to a distance past the outer circumference of the uppermost lamps and less than the outer circumference of the second lamps of the first and second rows;

a second vertical strip of the material located midway between the second lamps of the first and second rows, extending vertically, substantially from just less than the outer circumference of the second lamps;

a first light bar positioned adjacent the second and third lamps of the first row; and a second light bar positioned adjacent the second and third lamps of the second row.

11. The accelerated weathering apparatus of claim 10, wherein the barrier includes the first vertical strip, the first light bar and the second light bar.

12. The accelerated weathering apparatus of claim 9 further comprising:

a plurality of separately adjustable control channels for controlling outputs of the light sources, each of the channels controlling an output of at least one of the light sources.

13. The accelerated weathering apparatus according to claim 9, further comprising:

a power source for powering the light sources;

a ballast means connected to the light sources, for controlling the amount of power the light sources receive from the power source;

a controller, connected to the ballast means, to produce a ballast control signal for controlling operation of the ballast means;

a set-point means connected to the controller for generating and sending a set-point signal to the controller, the set-point signal determining an initial set-point value of the ballast control signal;

a light source detector means inserted into the specimen supporting means for detecting irradiance existing in the test chamber, and for generating an irradiance signal representative of the detected irradiance;

an irradiance signal input means for inputting the irradiance signal to the controller, the controller using the irradiance signal to adjust the ballast control signal, to maintain the selected set-point value; and, a calibration device, including a reference detector means designed to detect the irradiance inside the test chamber and to produce a reference irradiance signal representative of the detected irradiance, a reference irradiance signal transmitting means connected to the reference detector means, a calibration meter arranged for receiving the reference irradiance signal and for producing a calibration signal, and a calibration signal input means connected to the controller for inputting the calibration signal directly to the controller.

14. An accelerated weathering apparatus comprising:
a test chamber;
a specimen supporting means for supporting a specimen in the test chamber;
an array of light sources located within the test chamber for producing light in the test chamber;
a power source for powering the light sources; and,
a plurality of automatically adjustable control channels for concurrently controlling outputs of the light sources, each of the channels controlling an output of at least one of the light sources, the plurality of automatically adjustable control channels including a plurality of light source detectors arranged to detect different spatial areas of the specimen supporting means.

15. The accelerated weathering apparatus of claim 14, wherein each control channel further includes:
a ballast means connected to the at least one light source, for controlling the amount of power the at least one light source receives from the power source;
a control means, connected to the ballast means, for producing a ballast control signal for controlling operation of the ballast means;
a light source detector means of the plurality of light source detectors, the light source detector means inserted into the specimen supporting wall at a location corresponding to the at least one light source, to detect irradiance existing in the test chamber produced by the at least one light source, and for generating an irradiance signal representative of the detected irradiance;
an irradiance signal transmitting means connected to the light source detector means; and,
an irradiance signal input means for inputting the irradiance signal to the control means, the control means using the irradiance signal to adjust the ballast control signal, to maintain a selected value.

16. The accelerated weathering apparatus of claim 14, wherein there are first and second specimen supporting walls and there are first and second rows of light sources each row having four discharge lamps.

17. The accelerated weathering apparatus of claim 16, wherein the light source detector mean consists of four light source detectors inserted into the first and second specimen supporting walls such that each one of the four detectors is positioned to substantially detect irradiance form two of the discharge lamps.

18. The accelerated weathering apparatus of claim 17, wherein there are four separately adjustable control channels.

19. The accelerated weathering apparatus of claim 14 further including:
a calibration device, including a reference detector means designed to detect the irradiance inside the test chamber and to produce a reference irradiance signal representative of the detected irradiance, a reference irradiance signal transmitting means connected to the reference detector means, a calibration meter for receiving the reference irradiance signal and for producing a calibration signal, and a calibration signal input means for inputting the calibration signal directly to the controller.

20. The accelerated weathering apparatus of claim 14 further including:
a barrier located within the test chamber, composed of a material which interferes with a passage of the light produced by the discharge lamps in a pattern selected to increase an even distribution of light to the specimen supporting means.

21. A method of accelerated weather testing of specimens in a testing apparatus having a test chamber, a specimen supporting means, light sources powered by a power source controlled by a ballast, a plurality of automatically adjustable control channels for concurrently controlling outputs of the light sources, each of the channels controlling an output of at least one of the light sources, each channel having a light source detector, to detect the irradiance inside the test chamber, the method comprising the steps of:
detecting with each of the light source detectors irradiance existing int he test chamber substantially due to irradiance produced by the light sources associated with the control channel with which the light source is associated, in order to develop an irradiance signal;
transferring the irradiance signal detected by the ultraviolet detector to control circuitry of the control channel;
comparing the irradiance signal with a set-point value to determine if they are equal;
increasing a ballast control signal to the ballast associated with control channel when the set-point signal is greater than the irradiance signal;
decreasing the ballast control signal sequence to the ballast associated with the control channel when the set-point signal is less than the irradiance signal;
altering the ballast output associated with the control channel, based on the increase and decreasing steps in order to alter the output of the light source;
inserting a reference detector immediately adjacent one of the light source detectors;
selecting one of the control channels for calibration;
detecting with the reference detector irradiance existing in the test chamber substantially due to irradiance produced by the light source associated with the selected control channel, in order to develop a calibration signal;
comparing the calibration signal with the irradiance signal developed for the light source associated with the selected control channel; and,
outputting a signal to the ballast associated with the selected control channel in order to calibrate the output of the selected control channel.

* * * * *